United States Patent [19]
Reiss

[11] 4,081,689
[45] Mar. 28, 1978

[54] RADIOACTIVE SHIELDING MATERIAL

[75] Inventor: Meyer M. Reiss, Center Moriches, N.Y.

[73] Assignee: Atomic Products Corporation, Center Moriches, N.Y.

[21] Appl. No.: 724,116

[22] Filed: Sep. 17, 1976

[51] Int. Cl.² ............................................. G21C 11/00
[52] U.S. Cl. ................................................... 250/515
[58] Field of Search ................ 250/432 PD, 506, 515; 128/1.1, 215, 272.3

[56] References Cited

U.S. PATENT DOCUMENTS

| | | | |
|---|---|---|---|
| 3,973,554 | 8/1976 | Tipton | 250/506 X |
| 3,993,063 | 11/1976 | Larrabee | 250/515 X |

*Primary Examiner*—Davis L. Willis
*Attorney, Agent, or Firm*—Charles E. Temko

[57] ABSTRACT

A radioactive shielding material formed by coating or plating depleted uranium U-238 with a layer of beta ray impermeable material. The material has particular application for use as a hypodermic syringe shield component, and as shields for other hand held instruments carrying or impregnated with radioactive materials.

3 Claims, 5 Drawing Figures

RADIOACTIVE SHIELDING MATERIAL

BACKGROUND OF THE INVENTION

It is well known in the art to provide removable shielding adapted to engage a hypodermic syringe in such manner as to surround the barrel thereof and thereby shield a user from radiation emanating from the radioactive contents of the syringe. Most such devices include a bayonet-type locking means at the upper end thereof adapted to engage the outwardly projecting syringe flanges formed integrally with the barrel thereof, and normally contacted by the fingers of the user during the discharge of the syringe. Prior art syringe shields also include a single shield barrel formed of lead which covers the major portion of the length of the barrel, leaving an exposed lower end thereof to permit determination of whether or not the syringe is loaded.

There are several disadvantages in the use of this construction. One is the substantial weight of the lead shielding, often heavier than the weight of the syringe itself, and tending to make manipulation of the syringe awkward. Another is the fact that the exposed lower end of the syringe is the point of greatest radiation, and it is normally exposed at all times. Further, in order to calibrate the radiopharmaceutical dose in the syringe, it is usually necessary to remove the syringe from engagement within the shield, and during this process the technician is fully exposed to radiation. While such radiation is not normally dangerous to a patient, it is to be appreciated that the technician using the syringe is exposed to similar radiation on a daily basis, the total accumulation of such radiation being inherently dangerous. The term dose calibration is intended to mean in this specification, the placing of a loaded syringe in the proximity of radiation measuring means, rather than the loading of the syringe to a predetermined volume. This dose calibration is preferably accomplished immediately before use, since the radioactive materials normally injected decay very rapidly, and often lose all effective strength over the course of several days.

There has recently been developed by Harold W. Tipton of the National Institute of Health, Bethesda, Maryland, an improved shield made in two parts, including an upper shield element arranged in telescopic fashion with respect to a lower shield element, the upper shield element being of lightweight metal, the lower being of very dense metal such as tantalum or tungsten. This structure permits the confining of shielding material in the area where radiation is greatest, namely at the lower end of the barrel, and the retraction of the lower shield for dose calibration without the necessity of completely removing the shield from the syringe. As might be expected, the cost of manufacture of such devices results in a very high unit cost, making desirable the substitution, where possible, of lower cost materials in the lower shield element. While lead is a possible material, its inherent softness and heavy weight make it undesirable for this purpose, particularly in view of the telescoping sliding relationship between the upper and lower shield elements, necessary in this construction.

It is known to employ depleted uranium 238 as a radioactive shielding material in relatively large shielding installations, such use being particularly suitable where any residual beta ray diffusion is relatively harmless. It will be appreciated, that where such material is used on a daily basis by humans, the cumulative effect of beta radiation is also dangerous.

SUMMARY OF THE INVENTION

Briefly stated, the invention contemplates the provision of an improved shielding material suitable for use, for example as a syringe shield component, in which the component is formed of depleted uranium 238, which, after shaping, has been coated with another material which is substantially impervious to beta ray penetration, such materials including brass, tungsten, tantalum and titanium. The coating may be quite thin, in the order of several thousandths of an inch, since the amount of beta ray radiation in depleted uranium 238 is relatively small. The depleted uranium, having served its initial purpose, is commercially available at relatively low cost, and may be suitably machined or otherwise formed using techniques applicable to heavy metals. The application of the coating may be by vacuum deposition or equivalent operations.

BRIEF DESCRIPTION OF THE DRAWING

In the drawing, to which reference will be made in the specification, similar reference characters have been employed to designate corresponding parts throughout the several views.

DETAILED DESCRIPTION OF THE DISCLOSED EMBODIMENTS

Figure 1:
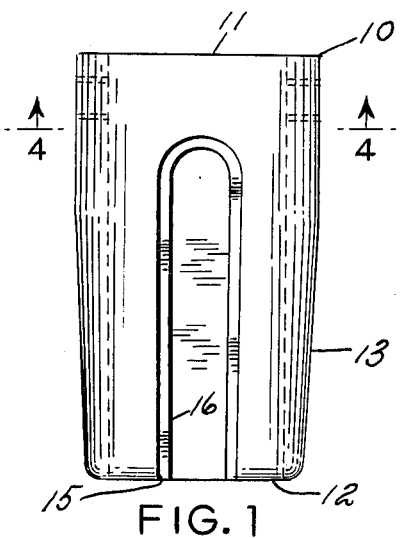
FIG. 1 is a side elevational view of an embodiment of the invention.
Figure 2:
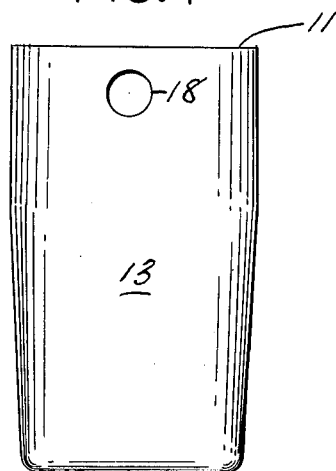
FIG. 2 is a side elevational view thereof, as seen from the side opposite that seen in FIG. 1.
Figure 3:
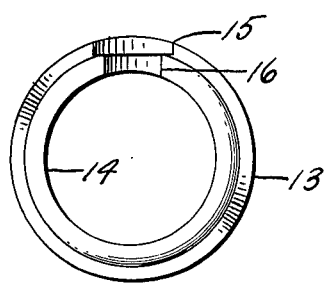
FIG. 3 is a bottom plan view thereof.

In accordance with the principal embodiment of the invention, the device, generally indicated by reference character 10 is in the form of a hollow sleeve or tube enabling it to be used as the lower shield element of a known retractable type shield for hypodermic syringes. The sleeve is formed by casting or machining from solid uranium 238, and is bounded by an upper end 11, a lower end 12, an outer cylindrical surface 13 and an inner cylindrical surface 14. A slotted opening 15 having a shoulder portion 16 thereof provides for a conventional lead glass window (not shown). A plurality of tapped bores, one of which is indicated by reference character 18 provides means for engaging the upper, relatively fixed sleeve element (not shown) comprising the syringe shield. For the contemplated use, the walls of the sleeve 10 are approximately 0.080 inches (3mm.) thick, as experimental use has shown that the additional degree of shielding obtained with wall thickness in excess of this amount is relatively insignificant.

Figure 4:
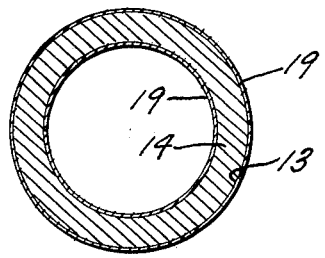
FIG. 4 is a transverse sectional view as seen from the plane 4—4 in FIG. 1.

Referring to FIG. 4 in the drawing, the entire device is coated with a layer of substantially uniform thickness varying between 0.010 inches and 0.015 inches using brass, steel, aluminum or tungsten. This may be accomplished by a known plasma spray method, by vacuum deposition techniques, or by conventional plating methods. The addition of 0.010 inches of brass plus 0.010 inches of tungsten as successive coatings was found more effective than the same amount of brass alone in reducing the beta surface exposure from depleted uranium.

The most commonly used radioisotopes used in nuclear medicine today are $^{99m}TC$ and $^{67}GA$. A comparison of the effectiveness of uranium as a shielding material compared with lead, tantalum and tungsten reveals a marked improvement. Uranium was found experimentally to be four times as effective as lead or tantalum in reducing radiation from $^{99m}TC$, and about 50% more effective than tungsten. When using $^{67}GA$ as the radioactive material, uranium was found to be 4.7 times as effective as tungsten, and over eight times as effective as lead or tantalum.

It is to be noted that the uranium 238 contemplated for shielding purposes is not a by-product from the reprocessing of spent reactor fuel rods, but is a "clean" residue of the known gaseous diffusion process wherein highly radioactive fissionable uranium 235 is separated from the less radioactive U-238.

Figure 5:
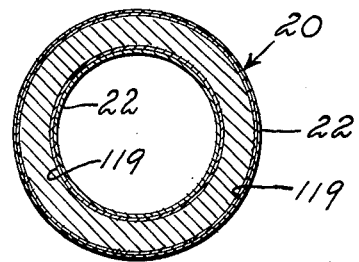
FIG. 5 is a sectional view corresponding that seen in FIG. 4, but showing an alternate form of the invention.

Although useful in the form shown in FIG. 4, a modified form illustrated in FIG. 5 is preferable. In this form, generally indicated by reference character 20, parts corresponding to those of the principal form have been designated by similar reference characters with the additional prefix "1".

In addition, a thin coating indicated by reference character 22 has been applied over the tungsten coating 19 in the form of a sprayed film of nylon of thickness ranging from 0.0035 to 0.005 to provide lubricative properties permitting the device 10 to be easily slid within the confines of the upper shield element of the retractable syringe shield of which it forms a part. By applying the coating to both the inner and outer surfaces of the device, the syringe itself may be more smoothly engaged owing to a reduction of sliding friction encountered.

It is to be understood that it is not considered that the invention lies within the precise details of structure shown and set forth in this specification, for obvious modifications will occur to those skilled in the art to which the invention pertains.

What is claimed is:

1. A radiation shield for use in enclosing radioactive hand operated instrumentation consisting of a main body of shield material formed from depleted uranium 238, and a layer of material deposited upon an exposed surface of said main body, said layer being at least partially impervious to the passage of residual beta ray defusion from said main body.

2. A shield in accordance with claim 1, in which said layer is selected from the group of metals consisting of tungsten, tantalum, brass, steel and aluminum.

3. A shield in accordance with claim 1, in which two layers are deposited on the exposed surfaces of said main body, including a first layer of brass and a second layer of tungsten.

* * * * *